United States Patent
Pelssers et al.

(10) Patent No.: US 12,065,633 B2
(45) Date of Patent: Aug. 20, 2024

(54) CELL PRESERVATION OR CULTURING ARRANGEMENT

(71) Applicant: KONINKLIJKE PHILIPS N.V., Eindhoven (NL)

(72) Inventors: Eduard Gerard Marie Pelssers, Panningen (NL); Cornelis Petrus Hendriks, Eindhoven (NL); Reinhold Wimberger-Friedl, Waalre (NL); Mark Thomas Johnson, Arendok (NL); Achim Hilgers, Alsdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 605 days.

(21) Appl. No.: 16/756,231

(22) PCT Filed: Oct. 17, 2018

(86) PCT No.: PCT/EP2018/078456
§ 371 (c)(1),
(2) Date: Apr. 15, 2020

(87) PCT Pub. No.: WO2019/077003
PCT Pub. Date: Apr. 25, 2019

(65) Prior Publication Data
US 2020/0239825 A1    Jul. 30, 2020

(30) Foreign Application Priority Data

Oct. 19, 2017 (EP) .................................... 17197261

(51) Int. Cl.
*A01N 1/02* (2006.01)
*A61J 1/10* (2006.01)
(Continued)

(52) U.S. Cl.
CPC ........... *C12M 27/18* (2013.01); *A01N 1/0263* (2013.01); *A61J 1/10* (2013.01); *B01F 31/312* (2022.01);
(Continued)

(58) Field of Classification Search
CPC ...................................................... C12M 35/04
See application file for complete search history.

(56) References Cited

U.S. PATENT DOCUMENTS

| 4,665,740 A | 4/1987 | Ruehland |
| 6,719,449 B1 * | 4/2004 | Laugharn, Jr. .......... B01F 11/02 366/127 |

(Continued)

FOREIGN PATENT DOCUMENTS

| EP | 1990402 A1 | 11/2008 | |
| WO | WO-2016193412 A1 * | 12/2016 | ......... H01L 41/0926 |

OTHER PUBLICATIONS

International Search Report from PCT/EP2018/078456 mailed Jan. 17, 2019.

*Primary Examiner* — Liban M Hassan

(57) ABSTRACT

A biological cell preservation or culturing arrangement (20) comprises a chamber defining a fluid retaining space (30) for retaining in use a body of fluid (34) and a deformable membrane (36) in communication with the fluid retaining space, and being manipulable by an electroactive polymer actuator arrangement (38) to undergo a defined topology change to induce in the fluid a pattern of fluid flow by which fluid is exchanged between a sub-region (46) immediately proximal the deformable membrane and a sub-region (48) removed from the deformable membrane.

18 Claims, 8 Drawing Sheets

(51) Int. Cl.
 B01F 11/00 (2006.01)
 B01F 31/31 (2022.01)
 C12M 1/00 (2006.01)
 C12M 1/12 (2006.01)
 C12M 1/34 (2006.01)
 B01F 101/44 (2022.01)

(52) U.S. Cl.
 CPC ............ C12M 23/14 (2013.01); C12M 25/00 (2013.01); C12M 41/42 (2013.01); *B01F 2101/44* (2022.01)

(56) References Cited

U.S. PATENT DOCUMENTS

| | | |
|---|---|---|
| 7,052,594 B2 | 5/2006 | Pelrine et al. |
| 7,971,850 B2 | 7/2011 | Heim et al. |
| 8,313,941 B2 | 11/2012 | Takayama et al. |
| 9,791,850 B2 | 10/2017 | Yoshida et al. |
| 2010/0018584 A1 | 1/2010 | Bransky et al. |
| 2011/0250585 A1 | 10/2011 | Ingber et al. |
| 2012/0003709 A1* | 1/2012 | Fukui ................ C12N 11/00 435/173.9 |
| 2016/0158757 A1 | 6/2016 | Breinlinger et al. |
| 2016/0208944 A1 | 7/2016 | Muir et al. |
| 2016/0326477 A1 | 11/2016 | Fernandez et al. |
| 2017/0108626 A1 | 4/2017 | Bolis |
| 2017/0137768 A1 | 5/2017 | Cuiffi et al. |
| 2018/0138833 A1 | 5/2018 | Van Den Ende et al. |
| 2018/0282680 A1 | 10/2018 | Chang et al. |

* cited by examiner

CELL PRESERVATION OR CULTURING ARRANGEMENT

CROSS REFERENCE TO RELATED APPLICATIONS

This application is a U.S. national phase application of International Application No. PCT/EP2018/078456 filed on Oct. 17, 2018, which claims the benefit of EP Application Serial No. 17197261.5 filed on Oct. 19, 2017 and are incorporated herein by reference.

FIELD OF THE INVENTION

This invention relates to a cell preservation or culturing arrangement, for instance including organ-on-a-chip cell culturing arrangements or devices, or arrangements or devices for preserving or storing biological matter such as blood.

BACKGROUND OF THE INVENTION

When biological cells or micro-organisms are grown on a surface they consume nutrients, including dissolved gasses, and excrete metabolites. Without active exchange of liquid close to the surface with bulk liquid, only diffusion can supply nutrients from the bulk liquid, and only diffusion can transport metabolites away from the surface to the bulk. Diffusion is a slow and inefficient mechanism for nutrient and metabolite exchange. Hence cell growth can be limited by this diffusion process, limiting the supply of nutrients and limiting the removal of excretion metabolites which may be harmful at higher concentration (for instance yeast cells on a surface producing ethanol). Moreover, when several layers of cells are cultured, the cells in the lower layer will increasingly encounter difficulties in obtaining sufficient nutrients and in clearing harmful metabolites.

A related difficulty arises in cases where blood is donated, and/or where blood is being stored, or where blood is being used as a culturing medium in a cell culturing device. One variety of cells present in blood is that of platelets (or thrombocytes). Platelets are responsible for blood clotting and perform this function in the body by gathering at a site of broken skin, adhering to the skin and then activating, upon which they irreversibly change shape. When blood is removed from the body and stored, premature activation of the platelets can be triggered unless the blood is continually agitated. Without agitation therefore the viability of the blood is severely diminished, and furthermore coagulation can even occur.

To prevent this happening, among other things, sufficient oxygen must be supplied to the platelets, and sufficient Carbon dioxide removed. Consequently, where blood is stored in bags for instance, each bag has to be placed on a bulky shaker in a temperature controlled storage cabinet.

It is known that during transportation in particular, without agitation, platelets can be activated. Shakers have been developed to continuously agitate the platelets when contained in a storage bag. However these are bulky arrangements which are especially burdensome during transportation. It is also known that smooth surfaces promote activation of platelets. Consequently, the inner surface of blood bags is patterned.

Means is sought for enabling more effective or reliable culturing or preservation of biological cells where the cells are carried or otherwise surrounded by a fluid, which can mitigate the problems outlined above. In particular a solution which can offer more efficient fluidic exchange of gas or other substances to the cells without the need for bulky mechanical shakers is desired.

SUMMARY OF THE INVENTION

According to examples in accordance with an aspect of the invention, there is provided a biological cell preservation or culturing arrangement comprising: a chamber defining a fluid retaining space adapted in use to retain a volume of fluid and adapted in use to retain biological cells for preservation or culturing;
  an impermeable deformable membrane arranged within the chamber or defining a surface of the chamber;
  an electroactive polymer actuator arrangement, arranged to deform the deformable membrane with the membrane retaining its impermeability, the electroactive polymer actuator arrangement being controllable to effect a controlled change in a surface topology of the deformable membrane; and
  the deformable membrane being arranged such that in use said surface topology change is such as to impel a pattern of fluid flow within the volume of fluid, in which fluid is exchanged between a first sub-region immediately adjacent the deformable membrane and a second sub-region apart from the deformable membrane.

Embodiments of the invention are based on provision of a deforming membrane, driven by an arrangement of electroactive polymers (EAP) actuators, which is controllable to create a fluid flow within a fluid such that fluid is exchanged between the surface and a bulk region of the fluid. In this way, nutrients or oxygen can be efficiently supplied to cells or other matter disposed adjacent or proximal the deformable membrane, and waste products can be efficiently flushed away from such cells and into the bulk. This hence assists in promoting cell growth (including e.g. tissue or organ growth), and hence in the culturing of the cells, tissue or organs. In addition, in the case of blood, such flow creates an agitative effect upon blood, in particular blood close to the deformable membrane. Accordingly, effective agitation is created with a solution which is small in form factor, unobtrusive, and relatively low-cost. Activation of platelets and also coagulation can be avoided by the arrangement, and so the blood cells preserved.

By biological cell preservation or culturing arrangement may be meant an arrangement or device for use in growing, or culturing cells or tissue (including e.g. tissue extracted during biopsy), including e.g. an organ on a chip arrangement or device. The arrangement may additionally or alternatively be a device or arrangement for preserving biological cells, tissue or matter for instance for preserving blood (cells), for instance by preventing activation of platelets and/or coagulation of blood. The arrangement may be for preservation of biological cells or tissue, e.g. biopsy tissue extracted during biopsy.

The arrangement may comprise a controller configured to control the electroactive polymer actuator arrangement to effect said controlled change in a surface topology of the deformable membrane. A controller may be provided as part of the arrangement or in further examples, a controller may be external to the arrangement, with the electroactive polymer actuator arrangement adapted to be communicable with the external controller to permit controlling of the actuator arrangement.

In all descriptions which follow, reference to a controller should be construed as meaning a controller which may either be part of the biological cell preservation or culturing arrangement or which may be external to but communicable with the arrangement.

The arrangement comprises a chamber defining a fluid retaining space for retaining in use a body of fluid. Thus the chamber is adapted in use to hold, or enclose or prevent escape of at least a volume of fluid. Thus a localized body of fluid may be consistently contained by the chamber, which is important for cell culturing and preservation. The chamber thus provides a cell culturing or preservation chamber.

A deformable membrane is arranged either within the chamber or arranged so as to define in use a surface of the chamber, e.g. by forming part of a wall of the chamber, or part of a wall of at least the fluid retaining space defined by the chamber. In this way, the membrane is arranged in direct contact with fluid retained within the chamber, such that a controlled topology change of the membrane impels a fluid flow pattern within the fluid.

The deformable membrane may have a continuous laminar form. By this may be meant that the deformable membrane is a continuous or uninterrupted membrane, e.g. a non-perforated or non-punctuated membrane. The membrane may in this case form a continuous layer.

The chamber may be adapted such that the fluid flow patterns generated by the topology change are contained within the chamber. This facilitates efficient exchange of fluid between a region proximal the deformable membrane and the bulk. By retaining fluid within the chamber, fluid flows that are generated are contained within the chamber and are efficiently directed to facilitating fluidic exchange between the bulk and the membrane, rather than directed e.g. out of the chamber, which does not assist with efficient exchange with the bulk. Exchange with the bulk enables effective replenishment of nutrients to biological cells located at or near the deformable membrane, and effective flushing of waste products from cells at the deformable membrane.

The deformable membrane is an impermeable deformable membrane, by which is meant a fluid-impermeable membrane, being impermeable to fluid retained in use in the chamber. By impermeable is meant that fluid cannot pass through the membrane, from one side to the other. The membrane furthermore retains its fluid impermeability even upon deformation of the membrane by the electroactive polymer arrangement.

The fluid retaining space may in particular be defined by a single enclosed chamber, rather than e.g. a network of chambers.

The chamber may be a fluidically closed chamber for retaining said volume of fluid in use. By fluidically closed may be meant a chamber which in use is fluidically sealed, or is in use an encapsulated chamber, and/or at least being so closed as to prevented escape or exit of fluid upon deformation of the deformable membrane. Thus, the chamber defines in use a closed fluidic system.

The chamber may be closed in the sense of being fluidically isolated in use from any other fluidic chambers or reservoirs, so as to form its own closed fluidic system. The fluidically closed chamber defining the fluid retaining space may be an encapsulated chamber.

By providing the fluid retaining space as an interior region of a fluidically closed chamber, fluid flow patterns may be efficiently isolated or contained within the chamber itself. This provides more efficient exchange of fluid between the region adjacent the membrane and the bulk of the fluid. The chamber in accordance with these examples is preferably closed in a manner to prevent fluidic flows out of the chamber upon impelling of the fluid flow pattern.

The chamber may in alternative examples not be completely fluidically closed. The chamber may in examples be fluidically connected via an outflow gate to an overflow region for accommodating a portion of a total volume of fluid retainable in use by said retaining space. The outflow gate and chamber may be shaped or arranged such that a majority of the fluid contained in the retaining space is retained therein during use. Thus a majority volume of fluid may be retained in use within the fluid retaining space. An overflow region may permit movement of the deformable membrane into the retaining space in cases where the fluid retaining space is completely filled with fluid.

In examples, in use the fluid retaining space may be only partially filled with fluid, to thereby leave an air gap for accommodating displacement of fluid within the space by deformation of the deformable membrane.

In examples, the chamber or at least a bounding wall of the fluid retaining space may be flexible to permit accommodation of displaced fluid within the space, displaced by the deformable membrane.

Ratios of dimensions of the chamber may advantageously be selected to facilitate fluid flows which promote efficient fluidic exchange between the deformable membrane and the bulk. In particular, a ratio of a chamber dimension extending outwards (i.e. in a substantially perpendicular direction) from a surface of the deformable membrane to a dimension extending transversely to the surface of the deformable membrane may be rendered sufficiently large to enable generation of substantially outwardly directed fluid flows from the membrane (into the bulk) as opposed to transversely diverted fluid flows. The chamber of the present invention is hence distinguished from e.g. a channel wherein typically a diameter or height of the channel is small compared with the length.

For example, in (non-limiting) advantageous examples of the present invention, a ratio of a dimension of the chamber extending outwardly from (i.e. substantially perpendicularly to) the deformable membrane surface to a dimension extending transversely to the deformable membrane surface may be between 1:1 and 1:20, or between 1:2 and 1:10. This may be compared for instance to the equivalent typical such ratio for a channel-like arrangement which is typically anywhere between 1:50 and 1:500. In such cases, fluid flows directed away from a deformable membrane are baffled by the channel boundary and thereby diverted transversely. This fails to promote efficient exchange of fluid between the surface and a bulk.

In general, the fluid retaining space should at least be suitable for retaining a volume of liquid, and reference to fluid may be construed accordingly.

By 'culturing arrangement' may be meant in general an arrangement or device which is for promoting or supporting growth and nurturing of cells or an arrangement or device which is for promoting cell growth. By 'preservation arrangement' may be meant in general an arrangement or device to maintain or preserve cells in a live state such that they may be utilized at a later point in that live state.

The invention represents a divergent approach to the mechanisms employed in most microfluidic type systems for instance, where an exclusively laminar flow is created in which fluid is driven to flow in parallel along a surface or wall. In such flow, there is little mixing between the fluid being driven along the wall and fluid away from the wall, further into the bulk; the only exchange between these two fluidic regions is by diffusion. However, as noted above, diffusion is slow and inefficient as a means of fluidic transfer of material. The present invention departs from this approach in controlling an actuator arrangement to deform the deformable membrane in a manner to induce a flow in directions away from the membrane, thereby encouraging mixing and exchange of fluid (and therefore also nutrients and/or waste products carried in the fluid) between the membrane surface and the bulk fluid.

More particularly, embodiments of the present invention provide an actuator arrangement operable to manipulate the deformable membrane to deform in a controlled way such as to effect a particular, defined change in the surface topology of the membrane. This topological movement of the surface imparts upon fluid immediately adjacent the surface a defined pattern of force and pressure, thereby precipitating within the fluid a particular, correlated, pattern of fluid flow, directly related to the specific topological change effected. Accordingly, specific patterns of flow paths within the fluid can be created in a controllable manner through instigating in the deformable membrane an appropriate shift in surface topology.

For the avoidance of doubt, by 'topology' is meant generally the surface relief pattern of a surface or the contour profile of the surface.

Embodiments of the invention rely upon the surface topology change effecting a sufficiently powerful force upon the fluid to instigate a fluid flow pattern between the membrane surface and the bulk. This is possible in particular through the use of an actuator arrangement which employs electroactive polymers (EAPs). Electroactive polymers (EAPs) are a class of materials within the field of electrically responsive materials. EAPs can easily be manufactured into various shapes allowing easy integration into a large variety of systems. Particular advantages of EAPs include low power, small form factor, flexibility, noiseless operation, accuracy, the possibility of high resolution, fast response times, and cyclic actuation.

The use of EAPs in particular for the actuator arrangement provides the advantageous properties of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Due to the high stroke and force they are able to yield in such small form factor, EAPs are ideal for providing the function of deforming the deformable membrane in a controllable way so as to effect a defined topology change. The actuator arrangement may comprise a plurality of actuator elements, or may comprise e.g. a single layer of actuator material being shaped or constrained in a manner such as to enable a shaped actuation pattern to be created.

In accordance with any embodiment of the invention, a controller may be adapted to control said actuator arrangement so as to effect regular or recurrent changes in said surface topology of the membrane on an ongoing basis such as to create a fluid flow in which fluid is continuously or recurrently exchanged between the first and second subregions. The recurrent changes may be intermittent but regular changes in the topology, i.e. a discrete shift in topology of the surface occurring at regular intervals on an ongoing, regular basis. By providing continuous or ongoing surface shifts, ongoing fluid flows are generated between the surface and the bulk, thereby ensuring reliable exchange of nutrients and waste products between areas adjacent the membrane surface and the fluid bulk.

The deformable membrane may in examples at least partially bound or enclose the fluid retaining space. The deformable membrane may form at least a portion of an enclosing or bounding wall of the fluid retaining space. This provides an efficient arrangement since driving electronics and interconnections of an associated actuator arrangement may be provided on a reverse side of the surface, taking them outside of the fluid retaining space, avoiding the need to fluidically protect or isolate these elements. If provided on or as part of a wall of the space, the wall can provide useful structural support for the surface and/or the actuator arrangement.

In accordance with one or more sets of embodiments, the topology change effected by the actuator arrangement under the control of a controller, may comprise surface deformations of the membrane directed inward and outward of the fluid retaining space wherein the inward deformations are balanced volumetrically with the outward deformations such that there is a zero a net change in the volume of the fluid retaining space before and after the topology change.

By 'balanced volumetrically' is meant that the change in the volume subtended by deformations directed inward, toward the fluid retaining space, i.e. protrusions, is such as to equal the change in the volume subtended by deformations directed outward, away from the fluid retaining space, i.e. depressions. Equivalently, the change in the volume of protrusions directed inward toward the fluid retaining space (from the membrane) is balanced by the change in the volume of protrusions directed outward of or away from the fluid retaining space (from the membrane).

The deformable membrane may in some examples be deformed from a first, flat configuration to a second, undulating (or otherwise uneven) one. Alternatively, the membrane surface may for example be deformed to move from a first, undulating (uneven) surface profile, to a second, different, undulating profile, but wherein the net aggregate volume of the convex and the concave undulations do not change (where concave volume is added negatively and convex positively, or vice versa).

The effect of this configuration is to ensure that the deformation of the membrane effects no overall change in the volume of the fluid retaining space. This means that the arrangement is able to create fluid flows within the fluid retaining space, even where the space is fluidically sealed, and completely filed with liquid, leaving no air gaps into which liquid can expand. Due to the incompressibility of liquid, creating fluid flows in such conditions would normally not be possible, since to create the flows, some displacement of the boundaries of the space is necessary, to provide accommodation for fluid displaced within the bulk.

The novel solution provided by this set of embodiments solves this problem by controlling the surface topology change of the membrane such that displacement at the boundaries is effected (since the membrane at least partially bounds the fluid retaining space), but in a manner that is volumetrically balanced, so that the incompressibility of the fluid does inhibit movement of fluid, i.e. the change in the surface does not decrease the overall volume of the fluid retaining space, which would not be possible due to resulting resistive forces exerted by the fluid upon the surface. In addition, the volumetrically balanced topology change ensures that the overall volume of the space is not increased by the membrane topology change, which, in a sealed space, would result in vacuum effects within the space, thereby exerting strong forces within the space and potentially causing significant damage to cells being cultivated or preserved therein.

The actuator arrangement may comprise an array of actuator elements, each comprising an electroactive polymer. The array is preferably an ordered array, e.g. comprising linear rows or columns. However, other arrangements and configurations are of course also possible, e.g. curved lines of elements, or less ordered arrangements. An ordered array provides the advantage of enabling the greatest flexibility as to the shape of topology change which can be created.

In preferred examples, each actuator element may be actuable to undergo a bending action. The bending action may be an out-of-plane actuation. The bending action may thereby effect an out of plane deformation of the deformable membrane in the region of the actuator element, in a direction generally outward of the surface and inward toward the volume of fluid. In this way, a surface topology change (i.e. a change in the surface relief pattern) can be effected where an array of such actuators is provided and so configured.

Each actuator element may be anchored at opposing sides such as to be actuable to undergo said bending action. EAP actuator elements may typically undergo in-plane deformation when electrically stimulated. The anchoring restrains the actuator at its edges thereby forcing the in-plane deformation outward to effect a bending action.

In particular examples, the electroactive polymer actuator arrangement may comprise an actuating layer, the actuating layer comprising said array of actuator elements. The layer may for instance be disposed adjacent to the deformable membrane, in engaging fashion, for instance beneath the deformable membrane to enable physical manipulation of the membrane by the actuator elements. This may provide efficient transfer of force from the elements to the membrane, and provide a compact arrangement. Other arrangements however are also possible.

The actuating layer may be a carrier layer carrying the array of actuator elements. The actuating layer may embody the actuator elements; i.e. the actuator elements may be integrally comprised by the actuating layer. The layer in this case may be a passive layer enveloping the actuator elements or at least covering the actuator elements for protection or electrical insulation.

Optionally, the actuator arrangement may comprise a layer of electroactive polymer material and wherein each actuator element comprises a segment of the layer of electroactive polymer. In this case the layer forms the actuator elements.

The layer may be segmented by forming partial breaks in the layer, such that each segment is controllable to undergo an individual bending action.

The layer may additionally or alternatively be segmented by anchors or clamps or pins provided anchoring local points or lines of the layer, such that segments of the layer between said anchors, clamps or pins undergo a bending action outward of the surface. Providing a single segmented EAP layer may represent the simplest arrangement in terms of ease of fabrication; providing one layer being segmented may be less time consuming and burdensome than separately forming a plurality of individual actuator element. This is especially the case where bending action is desired such that each may need to be configured with an individual clamping arrangement restraining its edges.

In accordance with one or more embodiments, each actuator element may be electrically drivable to move between a first stable actuation position and a second stable actuation position. By stable is meant that the actuator elements require a drive signal only to transition from one position to the next and then remain stable at that position in the absence of any further drive signal. Bi-stability is achieved by providing an actuator member formed of an EAP layer coupled to a resilient carrier layer, the actuator member being held constrained in a bent configuration by a clamping arrangement. Driving of the EAP layer with an electrical stimulus causes the actuator member to deform, causing it to flip or switch within the clamping arrangement from a first bent configuration to an alternate bent configuration.

Full details of this bi-stable actuator arrangement are provided in WO2016193412 A1.

This arrangement provides a particularly simple configuration for driving the change in topology. Current or voltage need only be applied when changing each actuator element between actuation positions; once the position is changed, the signal can be removed. Each element has just two stable positions, limiting the number of possible configurations, so reducing the complexity of the associated drive electronics and control thereof.

This configuration may be useful when driving recurrent, regular changes in the surface topology so as to effect an ongoing or continuous exchange of fluid. The membrane may for instance be recurrently alternated between a first surface topology, with actuation elements in a first varied set of positions, and a second surface topology, with each of the elements switched to their alternate positions. This configuration may also be useful for effecting the volumetrically balanced membrane surface deformation, by for instance simply alternating between a surface arrangement having elements in a first varied set of actuation positions to one in which each element is switched to its second actuation position. Thus, for each change of an element in one direction, there is a balanced change of another element in the opposite direction.

The biological cell preservation or culturing arrangement is generally suitable for use in any application in which reliable fluid exchange between a surface and a bulk region of a volume of fluid is useful for encouraging cell preservation or cultivation. Particular envisaged applications include arrangements dedicated to cultivating cells, and arrangements for storing blood.

Accordingly, in accordance with at least one set of embodiments, the arrangement is a cell culturing arrangement, and wherein the pattern of fluid flow is for enabling nutrient replenishment of cells located at or proximal to the deformable membrane.

By cell culturing arrangement is meant an arrangement or device for culturing biological cells, including for instance for culturing or growing tissue. The arrangement may for instance be for culturing biopsy tissue obtained by biopsy. The arrangement may for instance be for culturing or growing organ tissue or for culturing or growing organs. The arrangement may for instance be for organ-on-a-chip growth or culturing.

The biological cell preservation or culturing device may comprise a substrate for culturing biological cells, the substrate being arranged within the chamber. Optionally, the substrate may be adapted to retain the cells in fixed position on the substrate. This avoids the membrane surface deformation displacing or disturbing the cells.

In examples, the substrate may be comprised by the deformable membrane.

For example, the deformable membrane may be covered by an isolator (or insulating) coating. This coating might in examples constitute a substrate. Alternatively, a dedicated (e.g. flexible) substrate may be disposed coupled across a surface of the deformable membrane. In further examples, the deformable membrane may be shaped to delimit a non-actuating region or space, surrounded by the membrane, for accommodating a substrate.

The substrate may form at least part of a chip for organ-on-a-chip cell growth. Organ-on-a-chip is a term of the art generally denoting a chip, most usually one having means to permit movement of fluid over the chip, and means more generally for simulating activities, mechanics and physiological response of organs and organ systems. It is an emerging technology area in which initial breakthroughs have been made, but in which much work remains to be done, particularly in refining the microfluidic mechanisms for more efficient nutrient supply.

In accordance with at least one further set of embodiments, the arrangement may be a blood storage arrangement or device and wherein the deformable membrane is for agitating blood stored within the fluid retaining space to prevent activation of platelets within the blood and/or to prevent coagulation of the blood.

Optionally, the blood storage arrangement may comprise a blood storage bag, the bag forming said chamber of the arrangement. By 'bag' is meant generally a flexible container, or otherwise an enclosure bounded by a flexible outer skin. A bag may mean a fluidically sealed encapsulation, encapsulated by flexible walls, being e.g. formed of plastics materials.

The deformable membrane may in examples form at least a portion of an enclosing wall of the fluid retaining space of the blood storage arrangement. Optionally, the actuator arrangement may comprise an actuation layer comprising an electroactive polymer, the layer being disposed against said deformable membrane forming a wall of the fluid retaining space for deforming said membrane.

This provides an economical means of implementing the invention for blood storage bags. Blood storage bags are disposed of after a single use to avoid contamination. If the actuator arrangement were incorporated into the wall of the bag itself, this could prove costly since the actuators and electronics would need to be thrown away with each bag. Instead, these embodiments provide an arrangement in which the actuator arrangement is external to the bag, implemented in the form of a layer which can be applied or pressed against the deformable membrane for deforming it. This may simply be a fixed surface or layer on which the bag can be laid, or against which it can be hung or pressed. The bag can then be removed from the actuation layer when it is required for use, and the layer re-used for a different bag.

The actuation layer may be disposed against the deformable membrane in conformal fashion (i.e. so that the two surfaces conform to one another).

By 'enclosing wall' may be meant a fluidically encapsulating wall.

In examples, the blood storage arrangement may comprise two deformable membranes, each forming at least a portion of an enclosing wall of the fluid retaining space, and wherein each is arranged relative to a respective electroactive polymer actuator arrangement for deforming by the actuator arrangement.

In alternative examples, the electroactive polymer actuator arrangement may be comprised by or incorporated in or fixedly coupled to a deformable membrane forming at least part of a wall of the chamber or the fluid retaining space. Hence a blood bag may comprise or include the EAP actuator arrangement for deforming the deformable membrane.

In certain examples, there may be provided a cell culturing arrangement or device configured for retaining blood as a culturing medium. In these examples, the arrangement advantageously provides the dual function of facilitating efficient exchange of nutrients between the bulk and a wall of the chamber and facilitating agitation of the blood culturing medium to prevent activation of the platelets and coagulation of blood.

In preferred examples in accordance with any embodiment of the invention, the electroactive polymer actuator arrangement may comprise electrostrictive electroactive polymer material.

The cell culturing or preservation arrangement may comprise a plurality of deformable membranes, each arranged to be deformed by a respective electroactive polymer actuator arrangement, the plurality of deformable membranes being supported in separation from one another by a frame structure.

As noted above, the invention permits controlled generation of fluid flow patterns within the volume of fluid retained by the fluid retaining space. This is controlled by the particular topology change effected. These different fluid flows can be created by any embodiment of the invention By way of example, a controller may, in accordance with one or more examples, be adapted to control the actuator elements to actuate in sequential fashion, the actuation describing a sequential actuation path across the actuator arrangement, to thereby induce a wave-like fluid flow in at least a direction of said actuation path.

By way of a further examples, the controller may in accordance with one or more examples, be adapted to control the actuator elements to actuate in a cascading fashion wherein the actuators are actuated in sequential consecutive groups, each actuated group being larger than the previously actuated group.

Examples herein described also include a cell culturing or preservation arrangement, comprising: a biological cell culturing arrangement as described in examples above or as defined in claim of the present specification, and further comprising a volume of cell culturing fluid retained within said fluid retaining space; and/or comprising a blood storage arrangement as described in examples above or as defined in any corresponding claim, and further comprising a volume of blood retained within said fluid retaining space.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying schematic drawings, in which.

DETAILED DESCRIPTION OF THE EMBODIMENTS

Figure 1:
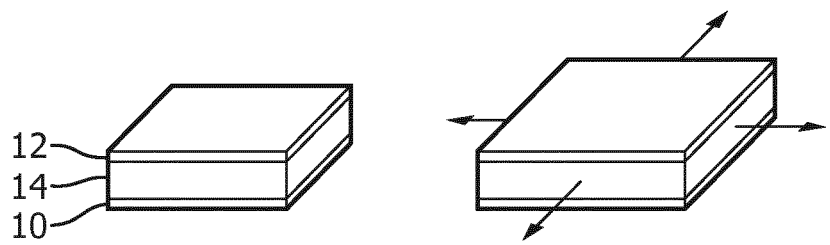
FIGS. 1 and 2 show two possible operating modes for an EAP device.

The invention provides a biological cell preservation or culturing arrangement comprising a chamber which defines a fluid retaining space for retaining in use a body of fluid, and a deformable membrane in mechanical communication with the fluid retaining space, and being manipulable by an electroactive polymer actuator arrangement to undergo a defined topology change to induce in the fluid a pattern of fluid flow by which fluid is exchanged between a sub-region immediately proximal the deformable membrane and a sub-region removed from the membrane.

Embodiments of the invention make use of electroactive polymers (EAPs) to facilitate actuation.

Electroactive polymers (EAPs) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP material give rise to applicability to new applications.

An EAP device can be used in any application in which a small amount of movement of a component or feature is desired, based on electric actuation. Similarly, the technology can be used for sensing small movements.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible.

Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field-driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field-driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field-driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrrole (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Altering the charge on the carbon atoms results in a change of C—C bond length. As a result, expansion and contraction of single CNT can be observed.

Figure 2:
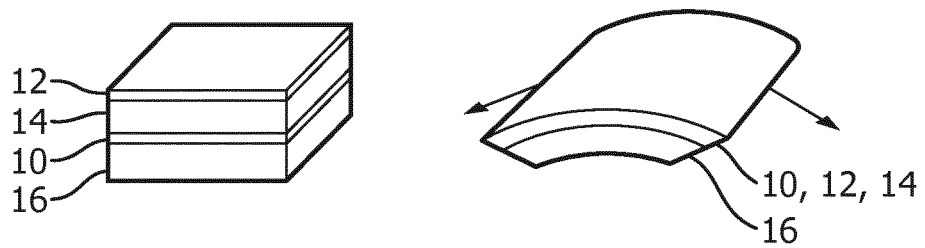

FIGS. 1 and 2 show two possible operating modes for an EAP device.

The device comprises an electroactive polymer layer 14 sandwiched between electrodes 10, 12 on opposite sides of the electroactive polymer layer 14.

FIG. 1 shows a device which is not clamped. A voltage is used to cause the electroactive polymer layer to expand in all directions as shown.

FIG. 2 shows a device which is designed so that the expansion arises only in one direction. The device is supported by a carrier layer 16. A voltage is used to cause the electroactive polymer layer to curve or bow.

Together, the electrodes, electroactive polymer layer, and carrier may be considered to constitute the overall electroactive polymer structure.

The nature of this movement for example arises from the interaction between the active layer, which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

An electroactive polymer structure as described above may be used both for actuation and for sensing. The most prominent sensing mechanisms are based on force measurements and strain detection. Dielectric elastomers, for example, can be easily stretched by an external force. By putting a low voltage on the sensor, the strain can be measured as a function of voltage (the voltage is a function of the area).

Another way of sensing with field-driven systems is measuring the capacitance-change directly or measuring changes in electrode resistance as a function of strain.

Piezoelectric and electrostrictive polymer sensors can generate an electric charge in response to applied mechanical stress (given that the amount of crystallinity is high enough to generate a detectable charge). Conjugated polymers can make use of the piezo-ionic effect (mechanical stress leads to exertion of ions). CNTs experience a change of charge on the CNT surface when exposed to stress, which can be measured. It has also been shown that the resistance of CNTs change when in contact with gaseous molecules (e.g. $O_2$, $NO_2$), making CNTs usable as gas detectors.

Embodiments of the invention make use of a deformable membrane which may in advantageous examples be part of an in-vitro culturing device or arrangement, for instance a so called organ-on-a-chip, or in further examples part of a storage container for blood or Platelets. A plurality of such membranes may in some examples be used, for instance comprising two surfaces, sealed at their peripheries to define a fluid retaining space there between which may be used as a collapsible container such as a blood bag.

Embodiments make use of electroactive polymer based actuation to deform the deformable membrane.

In certain examples, the deformable membrane may be composed of or comprise or otherwise carry electroactive polymer actuators, for instance electroactive polymer actuators for deforming the surface. The surface in further examples may be a thin, flexible layer or foil arranged over an actuating surface which comprises electroactive polymer actuators, for instance organized in a segmented manner for deforming the layer.

As such, a controllably deformable surface may be provided having a thin form factor, compared for instance to mechatronic or other electromechanical actuating means. The resulting arrangement has far smaller form factor for instance than a mechanical agitating or shaking arrangement for blood bags known in the art.

Figure 3:
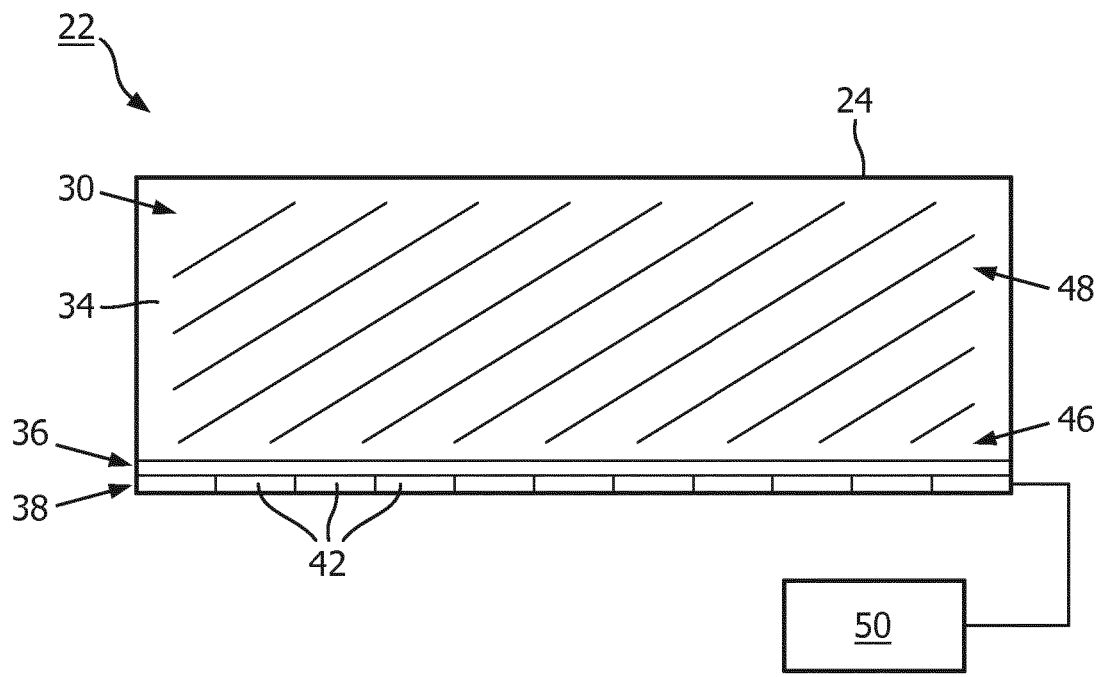
FIG. 3 shows an example biological cell preservation or culturing arrangement in accordance with one or more embodiments of the invention.

FIG. 3 illustrates a first example biological cell preservation or culturing arrangement in accordance with one or more embodiments of the invention. The arrangement 22 comprises a chamber 24, an internal cavity of which defines a fluid retaining space 30 for holding a volume of fluid 34 during use of the arrangement.

In mechanical communication with the fluid retaining space 30 is a deformable membrane 36. In the example of FIG. 3, the deformable membrane extends across a base of the chamber 24 to form one enclosing or sealing wall of the fluid retaining space. The deformable membrane is fluid impermeable. Coupled to an undersurface of the deformable membrane is an electroactive polymer (EAP) actuator arrangement 38, comprising an array of electroactive polymer actuating elements 42 being independently controllable by a controller 50 provided operatively coupled with the actuator arrangement. The controller is adapted to control the actuator arrangement to implement a controlled deformation of the deformable membrane to thereby induce one or more defined changes in a surface topology of the membrane.

Although in the particular example of FIG. 3, a controller is provided as part of the cell preservation or culturing arrangement itself, in further examples, a controller may be external to the arrangement, and wherein the actuator arrangement is adapted to be connected to and communicable with said external controller for controlling the actuator arrangement. All features, examples and descriptions which follow may be understood as implementable by an arrangement in which a controller is provided as part of the arrangement or in which a controller may be provided external to the arrangement.

Figure 4:
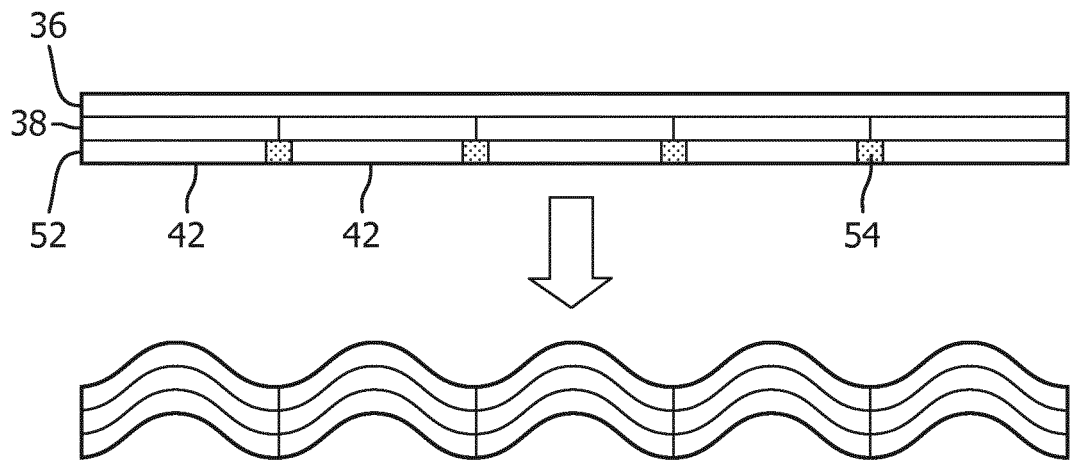
FIG. 4 illustrates the structure and operation of an example EAP actuator arrangement and deformable membrane in accordance with one or more embodiments.

FIG. 4 shows the deformable membrane 36 and EAP actuator arrangement 38 in more detail. The actuator arrangement in the present example comprises a continuous layer 38 of electroactive polymer (EAP) material coupled to a backing layer 52. The backing layer has greater flexural rigidity or resilience than the deformable membrane. Provided in array formation across the backing layer are a plurality of slits or anchoring elements 54 formed in, or coupled to, the backing layer. These slits or anchoring elements effectively segment the actuator arrangement 38, 52 into a plurality of individual actuator elements 42.

As shown in FIG. 4, upon electrical stimulation of the EAP material layer 38 by a current or voltage applied by an electrode arrangement (not shown), the EAP layer responds by in-plane deformation. The resilient backing layer 52 resists the in-plane deformation, thereby forcing out-of-plane deformation, or bending. The array of local slits or anchor points 54 break up the induced bending action into localized regions of bending, localized to regions subtended between the anchor points. Accordingly, each actuator element 42 undergoes a local bending action.

By applying electrical stimulation to only certain regions of the actuator arrangement 38, 52 covering only certain of the actuator elements 42, these actuator elements alone can be driven to actuate. Hence individualized control is possible of each actuator element. This may be facilitated in examples by segmented electrode arrangements, or by providing an individually drivable electrode arrangement for each actuator element.

By selectably controlling particular patterns of actuator elements 42 to deform, it can be seen that a controlled change in a surface topology of the deformable membrane 36 can be realised. Any particular topological pattern or profile can be created in the membrane through suitable driving of the actuator elements of the EAP actuator arrangement 38.

Figure 5:
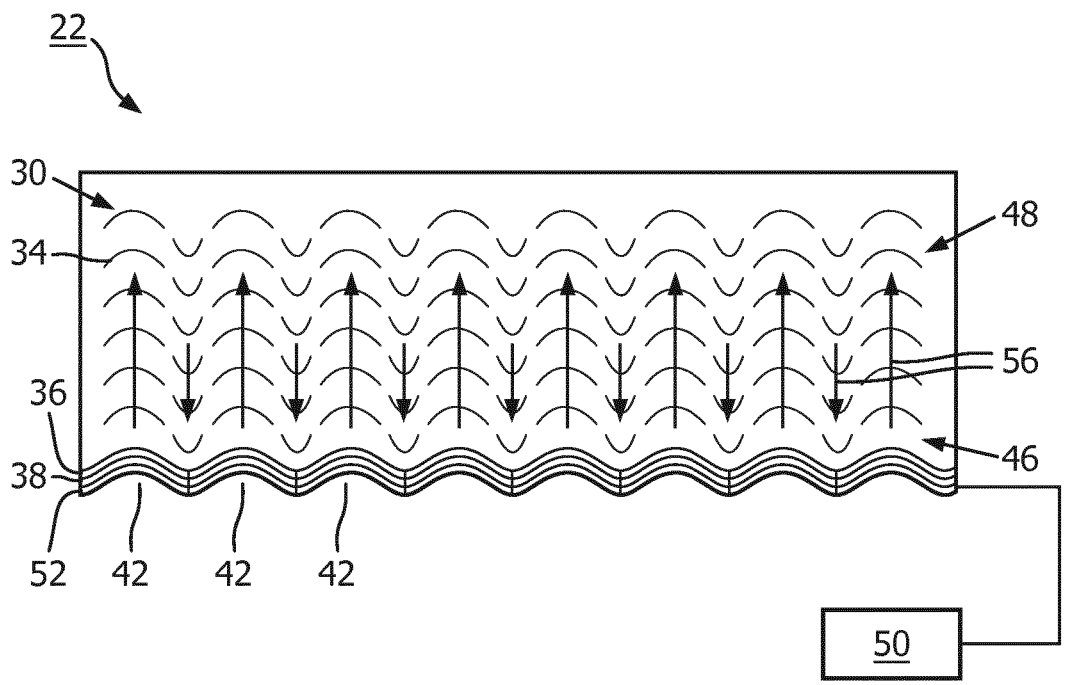
FIG. 5 shows operation of an example biological cell preservation or culturing arrangement in accordance with one or more embodiments in order to induce a fluid flow pattern.

As illustrated in FIG. 5, upon driving the actuator elements 42 to induce a change in the surface topology of the deformable membrane 36, a correlated pattern of fluid flow 56 is created within the fluid 34 of the fluid retaining space 30, by reason of contact with the membrane. Due to the out-of-plane directionality of the topology change, the fluid flow is in directions generally away from the deformable membrane surface. As a result, a fluid flow pattern is created in which fluid is exchanged between a first sub region 46 immediately adjacent or proximal to the deformable membrane and a second sub-region 48 more removed from the deformable membrane, i.e. in the fluid 34 bulk.

Many different fluid flow patterns may be created through suitable control. In certain examples, the change in surface topology is one which includes deformations in the membrane 36 directed both inward of the fluid retaining space 30 and outward from the fluid retaining space (as in FIG. 5). This represents a simple mechanism whereby fluid is induced to flow both toward and away from the deformable membrane, ensuring both supply of nutrients to the surface of the membrane and flushing of waste products away from the surface.

For the example of FIGS. 3-5, the actuator arrangement 38 is preferably controlled to recurrently deform the membrane 36 back and forth between a flat configuration and an undulating configuration, such as to provide efficient transfer of fluid both toward and away from the membrane.

The fluid retaining space 30 may in examples be fluidically sealed, and wherein the fluid is an incompressible liquid completely filling the space without any air pocket (or other gas). In this case, a surface topology change of the membrane 36 resulting in a net inward bending of the membrane (to the fluid retaining space) may only be possible if there exists some overflow means permitting temporary evacuation or accommodation of a portion of the fluid within the space, so that the membrane displacement can be volumetrically accommodated. The overflow means may be a further flexible membrane forming at least part of a sealing wall of the fluid retaining space, which membrane can bulge (outwardly directed with respect to the space) to accommodate the excess displaced fluid. This is necessitated by the incompressibility of a liquid. A bounding wall of the fluid retaining space or chamber may simply be flexible to accommodate displaced fluid in examples.

The overflow means may alternatively be provided by an overflow outlet of the fluid retaining space 30 (not shown) permitting temporary escape of fluid displaced by deformation of the deformable membrane 36 to for instance an overflow chamber. The outlet may in examples be provided by a permeable membrane element, comprising small fluid permeable holes to permit escape of fluid. The permeable membrane may preferably be provided with holes sufficiently small to prevent contamination by microorganisms.

Alternatively, overflow can be avoided in the deformable membrane by controlling a surface topology change which is volumetrically balanced between inward and outward directed deformations relative to the fluid retaining space 30. As a result, there is zero net change in a total volume of the fluid retaining space, as any local decrease in the volume by an inwardly bending actuator is balanced by a local increase by an outwardly bending actuator.

In examples, this may include moving from a flat membrane surface profile to an undulating profile, the undulation extending to equal linear displacement or amplitude on either side of a plane defined by the previous flat configuration.

In examples, the actuator elements 42 in accordance with this control example may be bi-stable electroactive polymer actuators, being drivable through application of a current or field to move between a first stable actuation position and a second stable actuation position.

By stable is meant that the actuator elements require a signal only to transition from one position to the next and then remain stable at that position in the absence of any further drive signal. Bi-stability is achieved by providing an actuator member formed of an EAP layer coupled to a resilient carrier layer, the actuator member being held constrained in a bent configuration by a clamping arrangement. Driving of the EAP layer with an electrical stimulus stimulates the actuator member to deform, causing it to flip within the clamping arrangement from a first bent configuration to an alternate bent configuration.

Full details of this bi-stable actuator arrangement are provided for instance in WO2016193412 A1.

By way of example, an actuator arrangement 38 may be moved from a first surface topology state in which substantially half of the actuator elements 42 are in a common first state (e.g. a flat state), and substantially half are in a common second state, (e.g. outwardly bending). The surface topology change may be effected by simply reversing the actuation states of each of the actuator element 42. Half will move to an outwardly bending state; the other half to a flat state, thus volumetrically balancing, allowing fluid flow lanes to be created, but without compressing the fluid.

In any example, the actuator elements 42 may be activated concurrently, either as a totality or in sub-groups, or may be activated individually or singly, for instance in an intermittent manner, to enhance mixing.

Advantageously, ratios of dimensions of the chamber in embodiments of the present invention may be selected so as to facilitate efficient mixing of fluid between a region 46 proximal the deformable membrane 36 and a region 48 in the bulk of the fluid.

For example, in (non-limiting) advantageous examples of the present invention, a ratio of a dimension of the chamber extending outwardly from (i.e. substantially perpendicularly to) the deformable membrane surface to a dimension extending transversely to the deformable membrane surface may be between 1:1 and 1:20, or between 1:2 and 1:10. This may be contrasted for instance with the equivalent typical such ratio for a (non-chamber) channel-like arrangement which is typically anywhere between 1:50 to 1:500. In such cases, fluid flows directed away from a deformable membrane are immediately baffled by the boundary of the channel, diverting the fluid transversely of the deformable membrane. This fails to promote efficient exchange of fluid between the membrane surface and a bulk.

By way of further illustration, an actuator element suitable for use in the present invention may by way of purely non-limiting illustration only have a maximum actuator displacement of approximately 70 micrometers (for an actuator element having a lateral width of 5 mm).

In accordance with one set of embodiments, the chamber of the arrangement may be a chamber formed by a blood bag. By way of non-limiting example, an example blood bag in accordance with embodiments the invention may have a "height", i.e. dimension between major surfaces of the bag, carrying the actuator elements, of approximately 30 mm.

Hence a typical ratio of a dimension of the chamber perpendicular the deformable surface to a maximum actuation displacement of the actuator elements may in non-limiting examples be in the order of 1:0.002, or for instance within the range 1:0.00015 and 1:0.002 for instance.

This may be contrasted for instance to a (non-chamber) blood carrying tube arrangement, wherein such a tube may have typical height of in the order of 4 mm. A ratio of channel height (perpendicular the deformable surface) to maximum actuator displacement may therefore be in the order of 1:0.02, i.e. in the order of a factor 10 smaller. A typical range of ratios may be from 1:0.00125 to 1:0.035 for instance.

The arrangement in accordance with one or more embodiments may provide a cell cultivation arrangement, e.g. an organ-on-a-chip arrangement. This may be a so-called 'tumor on a chip' arrangement. In non-limiting examples of such arrangements, a ratio of chamber height (generally perpendicular the deformable surface) to maximum actuator displacement may be in the order of 2700 micrometers to 70 micrometers, i.e. a ratio of in the order of 1:0.26 in non-limiting examples, or for instance within the range 1:0.0018 and 1:0.26 for instance.

This again may be contrasted with a channel like arrangement wherein the ratio between channel height and actuator displacement may be as small as 1:1. A typical range of ratios may be between 0.1 and 1 for instance.

It can therefore be seen that for the chamber arrangement of embodiments of the present invention, height:width ratios and height:actuator displacement ratios are generally larger than those of typical channel like arrangements.

A major difference between a channel and a chamber in the context of the present field is that a channel is used for continuous processes, while a chamber is used for batch wise (localized) processes.

For illustration the following processes may be performed in a channel: transporting substance(s) from one location to another location; mixing by transport using passive structures like a snakelike channel or special topology features in the channel; injecting two components in a channel and during transport a chemical reaction occurs between the components.

By contrast, and for non-limiting illustration only, the following may be performed in a chamber: mixing by active means; chemical reactions stimulated by mixing reactants.

In cases where a process requires a certain localized volume, a chamber is required, rather than a channel. This is the case for instance for cell culturing, containing a tissue culture, containing a tumor culture, or storing blood.

Storing blood in channels is not practical since this would dramatically increase the surface to volume ratio, significantly increasing the chance of adverse surface effects, i.e. activation of platelets on the surface or coagulation. In addition, a conduit of this kind would be more expensive than a blood bag, since the much larger surface area would necessitate a far greater quantity of actuation elements to sufficiently cover the surface to prevent platelet activation.

Furthermore, in the case of a cell cultivation arrangement or device used for growth of a tumor with angiogenesis, there is necessary a minimum channel height required to accommodate the outward growth of the tumor. A narrow chamber typically cannot accommodate growth of a tumor or e.g. an organ. In particular, spreading of the volume of the tumor widely so as to cover e.g. a single cell layer (so that it could fit within a channel) will not induce angiogenesis.

In particular, tumors can grow to a size of approximately 1-2 mm before their metabolic demands are restricted due to the diffusion limit of oxygen and nutrients. In order to grow beyond this size, the tumor switches to an angiogenic phenotype and attracts blood vessels from the surrounding stroma. This process is regulated by a variety of pro- and anti-angiogenic factors, and is a prerequisite for further outgrowth of the tumors.

As mentioned above, the actuator elements 42 may be addressed individually. Consequently, a wide range of different surface topology patterns and correlated fluid flows can be created. A range of fluid flow patterns which may be created will be described in embodiments below, and include 1) localized wave-like fluid flow across the deformable membrane 36, 2) global wave movement across the totality of the deformable membrane, thereby inducing large-scale exchange of fluid between the bulk and the membrane, and 3) local circular movement between a region proximal the membrane surface and liquid removed from the surface in the fluid bulk.

FIG. 6 illustrates an example control mode for controlling a surface topology change of the deformable membrane in order to induce a wave-like fluid flow pattern in the fluid 34. The controller 50 (not shown) is adapted in accordance with this mode to control the actuator elements 42 to actuate in sequential fashion, defining a sequential actuation path across the deformable membrane 36, to thereby induce a wave-like fluid flow in at least a direction of said actuation path.

Figure 6A:
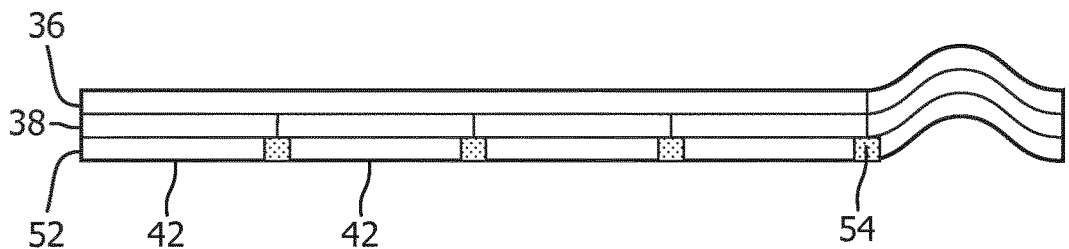
FIG. 6 illustrates an example control mode of an actuator arrangement in accordance with one or more embodiments.
Figure 6B:
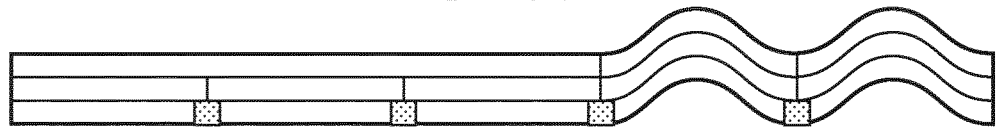
Figure 6C:
Figure 7A:
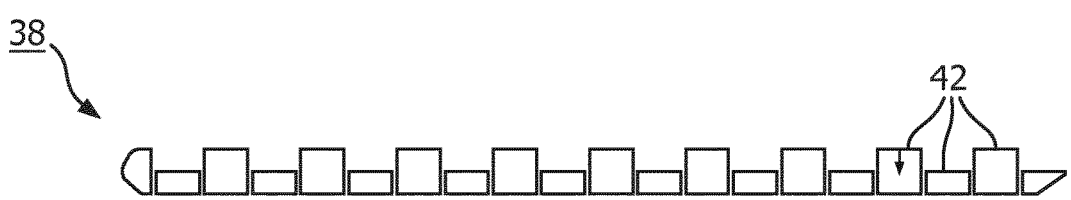
FIG. 7 shows a further example control mode of an actuator arrangement in accordance with one or more embodiments.
Figure 7B:
Figure 7C:
Figure 7D:
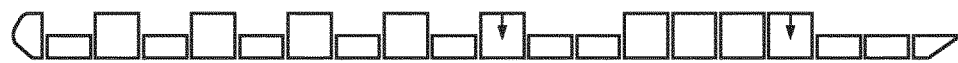
Figure 7E:
Figure 8A:
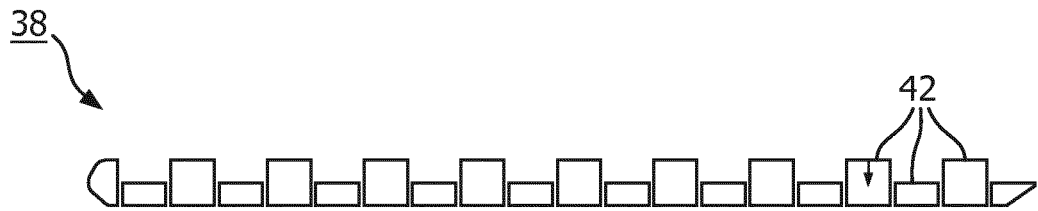
FIG. 8 shows a further example control mode of an actuator arrangement in accordance with one or more embodiments.
Figure 8B:
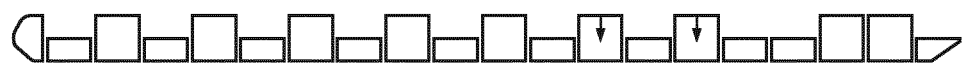
Figure 8C:
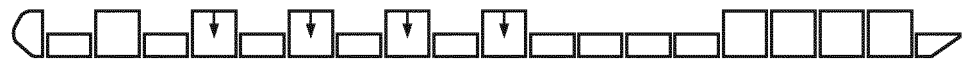
Figure 8D:
Figure 8E:
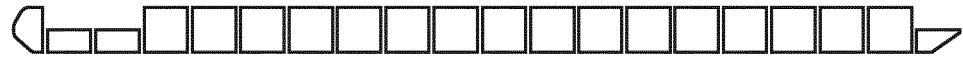

FIGS. 6(a)-(c) show the actuation at successive time points, at each of which a further single actuator element 42 has been sequentially activated. The elements are activated in the example from right to left. This generates a wave-like fluid flow over the membrane 36 surface from right to left.

In this example, in the non-activated state, the deformable membrane 36 is flat. In activated state, each actuator element 42 bends, and liquid 34 in the fluid retaining space 30 is pushed radially inwards towards the bulk region 48 away from the membrane surface (see FIG. 5). After the final (left-most) actuator has been activated, the actuators are deactivated in sequence from right to left, making a second wave over the surface. The start of a second wave may alternatively be started before the final (left-most) actuator has been activated.

Since there is a net flow over the surface to the left, this induces also a parallel leftward movement in the bulk liquid region 48, spatially removed from the membrane surface.

When the actuator elements are activated in sequence back from bent to flat configuration, a liquid flow back toward the deformable membrane 36 is effected. As in the example of FIG. 4, there are provided local slits or pinning points 54 in a backing 52 of the actuator arrangement 38 to segment the EAP layer 36 into localized actuator elements 42.

Although right-to-left activation is illustrated in FIG. 6, this is for illustration only. Any other directionality may also be implemented. The schematic illustration of FIG. 6 shows only a sectional view of the membrane layer. In reality a two-dimensional activation pattern is created across the surface. Hence the actuator elements may be activated in lines moving sequentially along the membrane surface, or activated individually across the surface in sequence.

As discussed above, a particular volumetrically balanced control scheme can be implemented for changing the surface topology of the deformable membrane 36 in order to provide fluid flow in an incompressible volume of fluid 36. In such a scheme, the created surface topology change comprises surface deformations of the membrane directed inward and outward of the fluid retaining space 30, where the inward deformations are balanced volumetrically with the outward deformations. The result is that there is a zero a net change in the volume of the fluid retaining space before and after the topology change.

FIG. 7 schematically illustrates such a control scheme.

In the example of FIG. 7, an electroactive polymer actuator arrangement 38 comprising an array of EAP actuator elements 42 is provided. These may be bi-stable actuator elements in preferred examples. In the figure, the actuator elements are shown as rectangles for simplicity of illustration.

The control scheme illustrated in FIG. 7 is to induce a wave-like fluid flow from right to left over the actuator arrangement 38 surface. The sequence of activation is shown by images (a)-(e), moving downward in time order. Each image shows a subsequent activation of actuator elements 42 as indicated by the small arrows. It can be seen that for each actuator element which collapses from an outwardly actuated state to a flat state, another element deforms in the opposite direction. Consequently, the total number of outwardly deformed actuators is the same at each point in time, and likewise for the non-outwardly deformed actuators. The net volume change in the volume of the fluid retaining space 30 is therefore zero.

The deformation pattern induces a sequential activation of the elements 42 moving from right to left. This creates the wave-like fluid flow while compensating any volume change by collapsing surrounding actuator elements at the same time.

FIG. 8 shows a further volumetrically balanced example control scheme for inducing fluid flow in an incompressible fluid.

In accordance with this control scheme, the controller is adapted to control the actuator elements to actuate in a cascading fashion wherein the actuators are actuated in sequential consecutive groups, each actuated group being larger than the previously actuated group.

As in the example of FIG. 7, a flexible surface 38 of bi-stable actuators is provided, represented schematically as rectangles in the illustration. A wave like liquid flow pattern is created in the fluid retaining space moving from right to left across the surface of the actuator arrangement 38. Each of FIGS. 7(*a*)-(*e*) shows a sequential stage in the actuation pattern. It can be seen that for each element actuated outward, another is collapsed flat, compensating the deformation volumetrically.

As can be noted, observing the pictures from (a) to (a), in each step an additional group of actuators is activated, being larger than the previously activated group. This causes a wave like avalanche flow from right to left.

As in previous examples, the illustration is schematic only, and only one portion of the actuator arrangement 38 surface is shown.

In accordance with a further set of example control modes, a surface topology change may be induced in the deformable membrane of such a pattern as to induce a cyclical or rotary movement of fluid within the fluid retaining space 30, circulating between a region 46 proximal the membrane surface and a bulk region 48 of the fluid 34.

Figure 9:
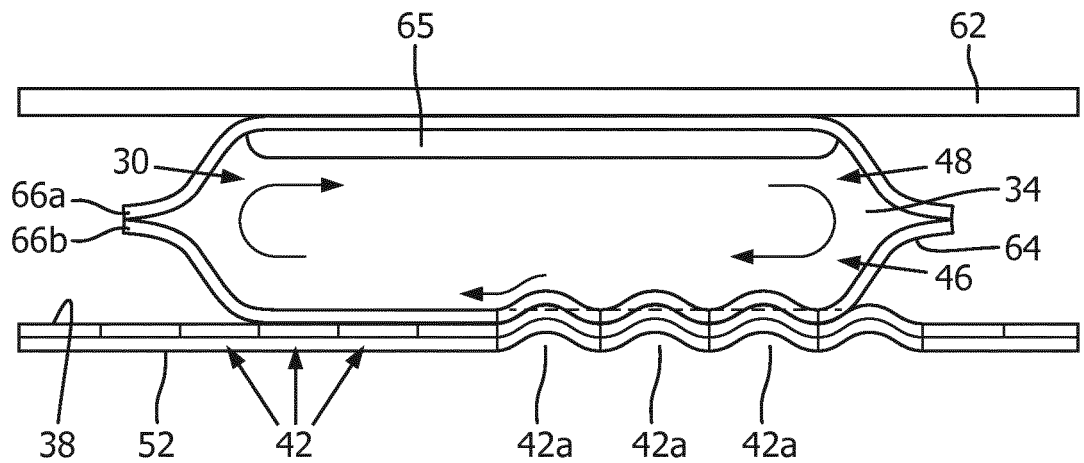
FIG. 9 illustrates structure and operation of an example biological cell preservation or culturing arrangement comprising a fluid retaining bag.

An example of this control scheme is illustrated in FIG. 9.

FIG. 9 shows by way of example a cell preservation arrangement comprising a bag 64 (e.g. a blood bag) which forms a chamber of the arrangement. The bag is formed from two flexible, deformable membranes or foils 66*a*, 66*b* joined at their peripheries to seal an inner fluid retaining space 30. The two membranes hence define respective surfaces or walls of the chamber. The bag is held between two parallel surfaces. The first (bottom) is an electroactive polymer actuator arrangement 38 coupled to a resilient backing layer 52 as described in previous examples. The actuator arrangement is disposed against the lower flexible membrane 66*b* of the bag in engaging fashion for deforming the membrane. The other of the parallel surfaces (upper) is a passive or static layer 62. The EAP actuator arrangement 38 may be provided mechanically clamped to the flexible foil 66*b* or otherwise releasably coupled, but need not be joined, sealed or fused to it. The actuator arrangement 38 is held in engaging fashion against the flexible foil 66*b*, such that the surface of the latter follows the topology change of the former.

In the example of FIG. 9, actuator elements 42 of the EAP actuator arrangement 38 are shown actuated sequentially from right to left, each actuated element 42*a* pushing on the flexible foil 66*b* of the bag to induce a corresponding surface deformation thereof. This surface deformation induces a consequent fluid displacement within the fluid retaining space 30 of the bag 64. The combined action over time of the sequence of actuated actuator elements 42*a* creates a particular fluid flow pattern within the bag 64. Due the shape of the bag 64 and the sequential actuation pattern, a cyclical fluid flow pattern is induced in the fluid retaining space 30, as indicated by the arrows. This cyclical flow circulates between a region 46 immediately proximal the lower flexible foil 66*b* and region 48 in the bulk of the fluid, removed from the foil.

In the present example, the fluid 34 in the fluid retaining space 30 comprises an air pocket 65 which can accommodate fluid 34 displaced by the bending pattern of the deformable foil 66*b*. This enables fluid flows to be realised without the requirement to balance surface deformations volumetrically as in the examples of FIGS. 7 and 8.

The bag 64 may be collapsible. The bag may be clamped between the two surfaces 62 and 36, 38. The upper surface 62 may be rigid or may be flexible.

The benefit of providing the active layer 38, 36 external to the fluid retaining space 30 such as to be only indirectly communicative with the fluid 34, via the deformable foil 66, is that the bag 64 may be disposed of separately, without destroying the actuating mechanism of the actuator arrangement 38. This is useful in the case that the bag provides the function of a blood bag. Blood bags can only be used once to avoid contamination. The arrangement of FIG. 9 allows the fluid of the bag to be actively agitated without the actuation mechanism being integral to the structure of the container itself.

Although in the illustrated examples, the number of actuating elements 42 extending across the bag surface is relatively few, this is for schematic illustration only. A larger number of actuator elements would typically be included in a surface extending across the side of the bag.

Although in the example of FIG. 9, an air pocket 65 is included to accommodate displacement of fluid 34 by deformation of the flexible foil wall 66*a*, in further examples, there can be implemented a volumetrically balanced control scheme (similar to those described in previous examples), and wherein a similar cyclical fluid flow pattern can be induced.

FIG. 10 shows an example in accordance with such a scheme.

FIGS. 10(*a*)-(*d*) show sequential actuation steps in a control scheme for inducing cyclical fluid flow in fluid 34 of a fluid retaining space 30, where there is no air pocket provided to accommodate fluid expansion.

The shown configuration comprises a bag 64 comprised, as in the example of FIG. 9, of two flexible foils 66a, 66b peripherally sealed together to define an inner fluid retaining space 30. The bag is disposed between a pair of parallel surfaces, each comprising a respective electroactive polymer actuator arrangement 38. Each electroactive polymer actuator arrangement is provided applied in engaging fashion to a respective one of the upper 66a and lower 66b flexible foils for inducing a surface topology change in the foils. The surface topology change induces a correlated fluid flow pattern within the fluid 34 of the fluid retaining space 30.

For the purposes of the present example, bi-stable EAP actuator elements 42 are assumed to be employed.

Figure 10A:
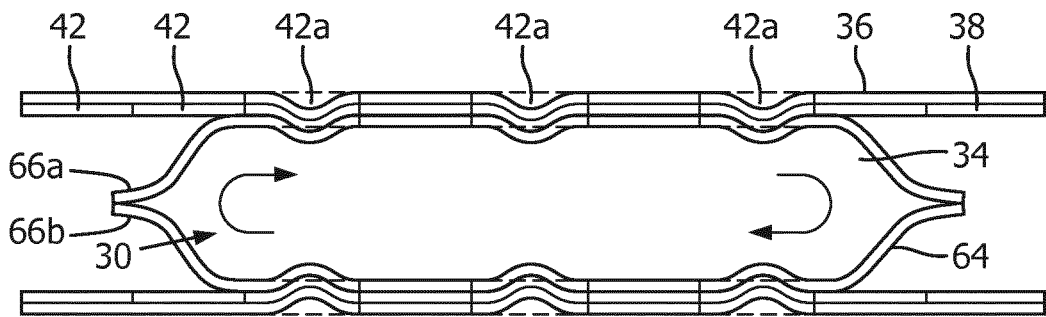
FIG. 10 illustrates a mode of controlling a biological cell preservation or culturing arrangement comprising a fluid retaining bag.

FIG. 10(a) shows an initial configuration of the actuator elements 42, where half of the elements are actuated 42a (also mirrored along the bottom surface), and half non-actuated.

Figure 10B:
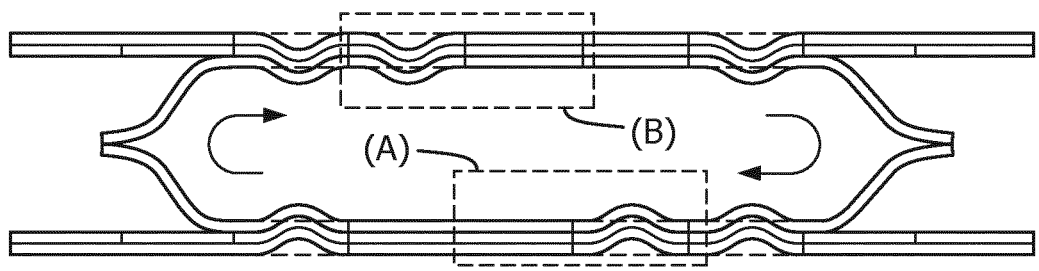

FIG. 10(b) shows a subsequent actuation state, wherein the total number of active and inactive actuator elements 42 has not changed, but their locations have moved. In particular, those elements enclosed by dashed lines are those whose actuation states have changed. Those indicated by (A) are switched first, with those indicated by (B) switched subsequently, after a short delay. By activating these sets separately, the desired cyclical flow is better induced (in this case a clockwise flow is created).

Figure 10C:
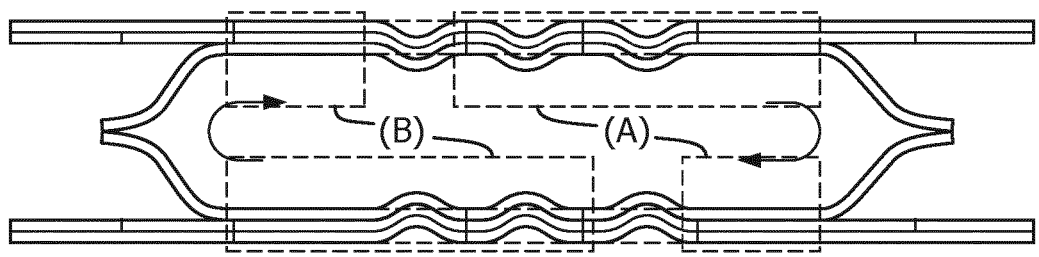

FIG. 10(c) shows the next actuation state. Again, actuator elements 42 shown circled by the dashed lines are those that have changed state, with those indicated by (A) changed first, followed by (B), again to maintain the desired cyclical flow.

Figure 10D:
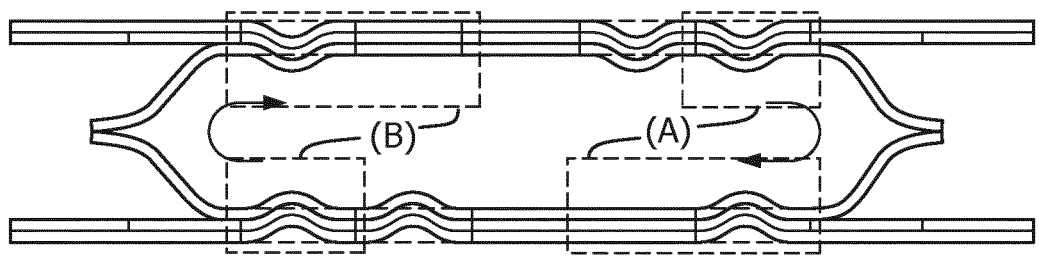

FIG. 10(d) shows a final actuation state, with again those actuators shown circled by dashed lines those that have changed actuation state, those indicated by (A) changed first, followed by (B).

The skilled person will readily recognize that continuation of this activation pattern would maintain the cyclical pattern of liquid flow.

An electronic circuit may in examples be provided, configured to control the pattern of actuator activation necessary to maintain the cyclical flow pattern, whilst also maintaining zero net change in the volume of the fluid retaining space 30. This may be achieved for example by means of a lookup table, being programmed with a sequential list of actuator states for each sequential stage; however other means can also be used.

FIG. 10 shows a sectional view only of the bag 64. It will be appreciated that cyclical motion in a transverse direction to that shown (i.e. into or out of the page) can also be created, through similar sequential control of the actuator elements 42 but configured in an altered orientational arrangement.

The use of dual actuator arrangements 38 and associated deformable membranes 66, as shown in FIG. 10, is not limited to application within or for a bag. Such a configuration may also be provided for a cell culturing arrangement, wherein two or more deformable membranes, each having an associated deforming EAP actuator arrangement may be assembled, for instance supported in separation from one another by means of a frame structure. Such an actuator arrangement may be used as part of an organ-on-a-chip arrangement in examples. The deformable membranes may form an integral part of the organ-on-a-chip arrangement or may be arranged engaged against a flexible foil being part of the arrangement.

By way purely of illustration an example blood bag in accordance with one or more embodiments of the present invention may typically have a fluid retaining space of volume capacity of 500 cm$^3$, and a surface area of approximately 15×10 cm. The average 'height' of the blood bag (distance between the major surfaces of the bag) may be in the order of ~3.3 cm, e.g. 3-5 cm.

Therefore, a typical aspect ratio (average length divided by height) may be around ((15+10)/2)/3.3, i.e., ~4. A typical example range may be between 1.8 and 8 for instance. In the case of a collapsible bag, around a central region of the bag, the height may be around 5 cm, this decreasing to zero at edges of the bag.

This may be contrasted with a (non-chamber) channel for instance, which may typically gave internal diameter of ~4 mm, with a length e.g. of approximately 50 cm, thereby giving an aspect ratio of around 50/0.4, i.e., ~125. A typical example range may be for instance between 62 and 500.

Hence it can be seen that the aspect ratio (length/height) is typically much smaller for chambers (in accordance with present invention) compared to channels. This smaller aspect ratio assists in the efficient exchange of fluid between the deformable membrane and the bulk, since the height of the chamber allows accommodation of free fluid flows in a direction outward of the deformable surface. In a channel, the restricted height means fluid flows are generally re-directed laterally along the channel.

As noted above, in embodiments of the present invention, a cell cultivation arrangement may be provided for culturing tumor growth. Tumors may, by way of illustration, grow to a volumetric size of approximately 5 mm$^3$, having e.g. (diametric) height ~1.34 mm. In preferred cases, the chamber of the cell culturing arrangement may have width (i.e. transverse the deformable surface) approximately two times larger than a height (i.e. perpendicular to the deformable membrane 36 surface) of the chamber. Hence an aspect ratio, (length divided by height) in this example case would be 2. A suitable example range of aspect ratios may be between 2 and 20.

By contrast, typical (non-chamber) micro channels in an organ-on-a-chip arrangement or device may typically have a length of approximately 5 mm and a diameter of approximately 50 micrometers, giving an aspect ratio (length/height) of approximately 5000/50=100. A typical example range may be for example between 50 and 200.

It can hence again be seen that the aspect ratio (length/height) is typically much smaller for chambers (in accordance with present invention) compared to channels. This smaller aspect ratio assists in the efficient exchange of fluid between the deformable membrane and the bulk.

It is emphasized that the above outlines example dimensions are ratios are purely illustrative and are not limiting to the concept of the invention.

Although in various examples outlined above, an actuator arrangement 38 is provided comprising a layer of EAP coupled to a resilient backing, in further alternative examples such a backing may be omitted. In such a case, a quasi-random bending configuration may be achieved upon electrical stimulation of the EAP layer. For instance, a wrinkling pattern may be induced. Here a similar, although less configurable, fluidic effect is realised in the fluid retaining space 30, wherein fluid is exchanged between a region 46 proximal the deformable membrane 36 and a region 48 removed from the deformable membrane, within the fluid bulk.

The controlled topology change of deformable membrane 36 may play a dual role in some embodiments. For embodiments providing a cell culturing arrangement, the topology change may provide useful mechanical stimulation of cells being cultured on a surface (e.g. a chip surface) carried by the deformable membrane.

This is of use for instance is simulating natural growing conditions for certain kinds of cells. For example, cells in Alveoli in the lungs are stretched in normal conditions. Cells of the heart are continually deformed or stretched by contractions of the heart. Hence mechanical stimulation of cells by the deformable membrane may usefully mimic in-vivo conditions of cell growth. It is well known that such mechanical stimuli may have a significant influence on cell culturing. For instance, culturing heart muscle cells requires such a mechanical stimulus in order to induce growth of a cell layer that exhibits the behavior of a muscle.

In accordance with one or more examples, a dedicated support structure for carrying culturing cells may be provided, said support structure having carrier surfaces being controllably deformable to permit controlled mechanical deformation of culturing cells. In examples, the structure may be deformable independently of the deformable membrane or may be mechanically or operatively coupled with the deformable membrane so that the deformable membrane stimulates deformation of the support structure.

In examples, the actuator arrangement 38 may comprise a mix of electroactive polymer and other kinds of responsive materials, or there may be provided additional actuator arrangements, being comprised of other responsive materials instead of EAPs. Responsive materials are a broader class of materials having properties of reversibly deforming or otherwise changing in structural properties in response to one or more electromagnetic stimuli. Varieties of responsive material include, by way of example, heat-responsive shape-memory materials, such as shape-memory alloys and shape memory polymers, magnetostrictive materials, magnetic shape memory alloys, piezoelectric materials, and photoresponsive materials (photomechanical materials). Optically responsive materials have particular benefits in certain cases, in particular where certain cells may be sensitive to the electrical signals used to stimulate the EAP material.

Examples described above include an EAP actuator arrangement being formed of or segmented into an array of individually deformable EAP actuator elements 42. The size of each actuator element may be chosen in accordance with the particular flow patterns that are required to be created.

Typical human cells are approximately 10-20 micrometers across and platelets are approximately 1-2 micrometers across. By way of example, actuators of 5 mm in width can achieve a linear (out-of-plane) displacement amplitude of 70 micrometers, which is sufficient to create a surface flow and to disturb depletion layers around biological cells. Since the created flow emanates from the deformed surface itself, fluid regions surrounding even cells being directly adjacent the surface are disturbed, both agitating cells and providing exchange of nutrients and waste products to and away from the cells. Hence platelets may be prevented from activating and these and other cells efficiently preserved and cultured with nutrients.

It should be noted that the dimensions of the fluid retaining space 30, in particular the distance from the deformable membrane 36 to any opposing boundary wall, will influence the flow pattern achieved by a particular surface topology change. A very narrow distance may result in a flow pattern which is diverted, via baffling with the opposing wall, in a direction substantially across the deformable membrane. A much greater separation distance may result in a flow pattern more perpendicularly directed relative to the membrane. A distance being such as to encourage the latter more perpendicularly directed flow may be preferred, since fluid exchange with the bulk may in this way be better promoted.

In accordance with one or more examples, the EAP actuator arrangement 38 may comprise or otherwise accommodate an inactive surface region in which no actuator elements 42 are provided or such actuator elements are not activated, such region being preferably located surrounded by active regions. The inactive region may accommodate biological cells for culturing and may comprise a membrane or substrate or chip carrying cells for culturing or to which cells may be adhered for culturing. A membrane may be provided covering cells and being permeable to nutrients. By providing the cells in an inactive region, potential damage by the topology change of the deformable membrane 36 can be avoided in the case of mechanically sensitive cells, while at the same time facilitating fluidic exchange between a region 46 directly adjacent the cells and the fluid bulk 48.

Furthermore, although in accordance with examples described above, an actuator arrangement 38 and deformable membrane 36 are provided which extend across the totality of the fluid retaining space 30, in further examples, the membrane or the actuator arrangement may extend only partially across the space, or may be localized to a central area of the base of the space, surrounded by fluid.

Above have been described schemes for accommodating displacement of fluid within the chamber by volumetrically balancing deformations of the actuator arrangement. By way of alternative, in the example of FIG. 9, displacement is accommodated by only partially filling the fluid retaining space 30 of the chamber with fluid, leaving an air gap 65 into which displaced fluid can move.

In accordance with further examples, an overflow means may alternatively be provided for temporarily accommodating fluid displaced by movement of the deformable membrane into the fluid retaining space 30 of the chamber.

In examples, the overflow means may comprise an overflow outlet or conduit extending from the chamber to an overflow space, permitting temporary evacuation of fluid from the main chamber.

Figure 11:
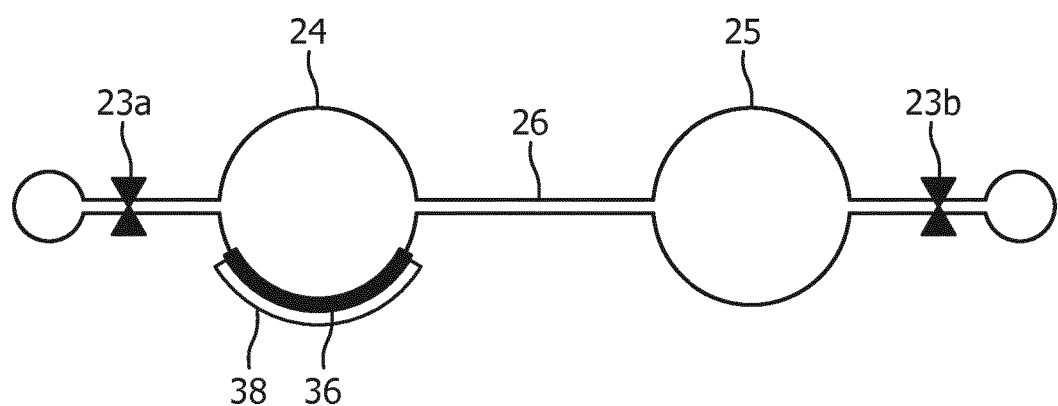
FIG. 11 schematically illustrates an example biological cell preservation or culturing arrangement in accordance with one or more embodiments.

FIG. 11 schematically illustrates an example of such an arrangement. The shown arrangement represents a cell-culturing arrangement in accordance with one or more embodiments of the invention. The arrangement may be an organ-on-a-chip arrangement in examples.

The arrangement comprises a main (incubation) chamber 24 for holding cells for culturing, the main chamber being fluidically connected via an overflow outlet 26 to a secondary overflow chamber 25 for accommodating fluid which may be displaced from the main chamber 24 upon deformation of the deformable membrane 36 of the main chamber. The deformable membrane 36 may define part of a wall of the main chamber or may be arranged within the main chamber, and in either case is adapted to be deformable to undergo a defined topology change.

The arrangement further comprises an electroactive polymer actuator arrangement 38 arranged in engaging relationship with the deformable membrane 36 for deforming the membrane and effecting a controlled topology change of the membrane as described in examples above.

A portion of a wall of the overflow chamber 25 may comprise a flexible foil or membrane, flexible to permit compensating of any volume changes induced by the electroactive polymer actuator arrangement 38 of the main chamber 24. The flexible foil or membrane may be comprised by an upper portion of the outer wall or boundary of the overflow chamber.

In use, an inflow valve 23a and outflow valve 23b of the arrangement are closed to prevent escape of fluid contained within the fluid retaining space of the arrangement. Displacement of fluid within the main chamber 24 by deformation of the deformable membrane 36 may flow through the overflow outlet 26 and be accommodated by the overflow chamber 25. Alternatively, both chambers may be filled with fluid, and wherein a deformable foil portion of the overflow chamber 25 is flexible to permit volumetric accommodation of fluid displaced within the main chamber by the deformable membrane 36.

The whole arrangement may be housed within a housing, the housing being closed by a lid. The housing may be a rigid structure.

In accordance with any embodiment or example described above it may generally be advantageous that different actuator elements 42 of the actuator arrangement are actuable independently of one another, for instance to be activated at different times, e.g. sequentially. Efficient driving circuity to achieve this is desirable, to avoid the need to provide individual wire connections to each actuator element and have an individual drive controller for each. This would be both expensive and complex. Any such added cost is particularly an issue for disposable arrangements.

In accordance with a first set of examples, actuator elements may be connected instead in a multiplexed or serial bus manner. In this case, a plurality of actuator elements are arranged as a linear set, by which is meant connected electrically in a line. Data for controlling the driving of the individual actuator elements is provided on a data line, and data line connections are made between each adjacent pair of actuator elements. The actuator elements are controlled in dependence upon received data from the data line.

Each actuator element comprises at least two power line terminals and at least one digital data line terminal. The arrangement includes at least two power lines and a data line, wherein each actuator element is connected in parallel between the at least two power lines, the at least two power lines connecting to the at least two power line terminals.

This approach represents some simplification, but still involves significant complexity and cost.

In accordance with a further, preferred, approach, individualized actuator control may be achieved by providing a driving electrode arrangement having independently controllable portions. For instance, electrodes disposed on at least one side of the actuator arrangement may be provided as interdigitated electrodes, or variants thereof. Such an arrangement makes it possible to independently control the stimulation applied to two different actuator elements without adding any further complexity in the form of, e.g. crossovers or vias.

In particular, interdigitated (e.g. comb-like) electrode structures use pairs of electrodes in the form of interdigitated combs (i.e. in the form of interlocking fingers). This allows an in-plane electrode arrangement, by establishing electric fields or currents for driving the actuator elements in-plane between fingers of the electrodes.

In examples, electrode arrangements on both sides of the actuator arrangement may be provided as such interdigitated comb type electrodes, or variants thereof. It now becomes possible to activate four actuator elements independently—two (in-plane) from one side of the actuator arrangement and two (in-plane) from the other side. During actuation by electrodes on one side, those on the other may provide reference electrodes to establish the electric field or complete the current across the EAP actuator elements. In this manner, it is possible to individually actuate 2×2 square arrangements of actuator elements 42 (where the comb electrodes on the two sides of the actuator arrangement are rotated 90 degrees with respect to one another). Alternatively a line of four adjacent electrodes may be individually actuated (if the comb electrodes on the two sides are arranged parallel with one another). The latter arrangement may be advantageous for creating wave-type flow patterns in the fluid retaining space 30.

Preferred arrangements for driving electronics of embodiments of the invention will now be described.

Described above are modes for controlling activation of actuator elements 42 in a sequential or otherwise non-concurrent manner. Complex electronics and complex driving schemes for implementing these and other control schemes may be avoided through a novel driving scheme described below.

As will be recognized by the skilled person, it is possible to drive each actuator element 42 by providing a separate control line or through implementing a 2D-matrix type approach, allowing activation of the actuator elements in the required order. However this would necessitate a very large number of wires and connections between the actuator arrangement 38 and the controller 50.

In accordance with a proposed driving scheme, a simple and inexpensive analogue electronic approach is provided to serially activate chains of actuator elements 42. In particular, each actuator element is triggered to actuate by its predecessor, after a variable time delay.

Figure 12:
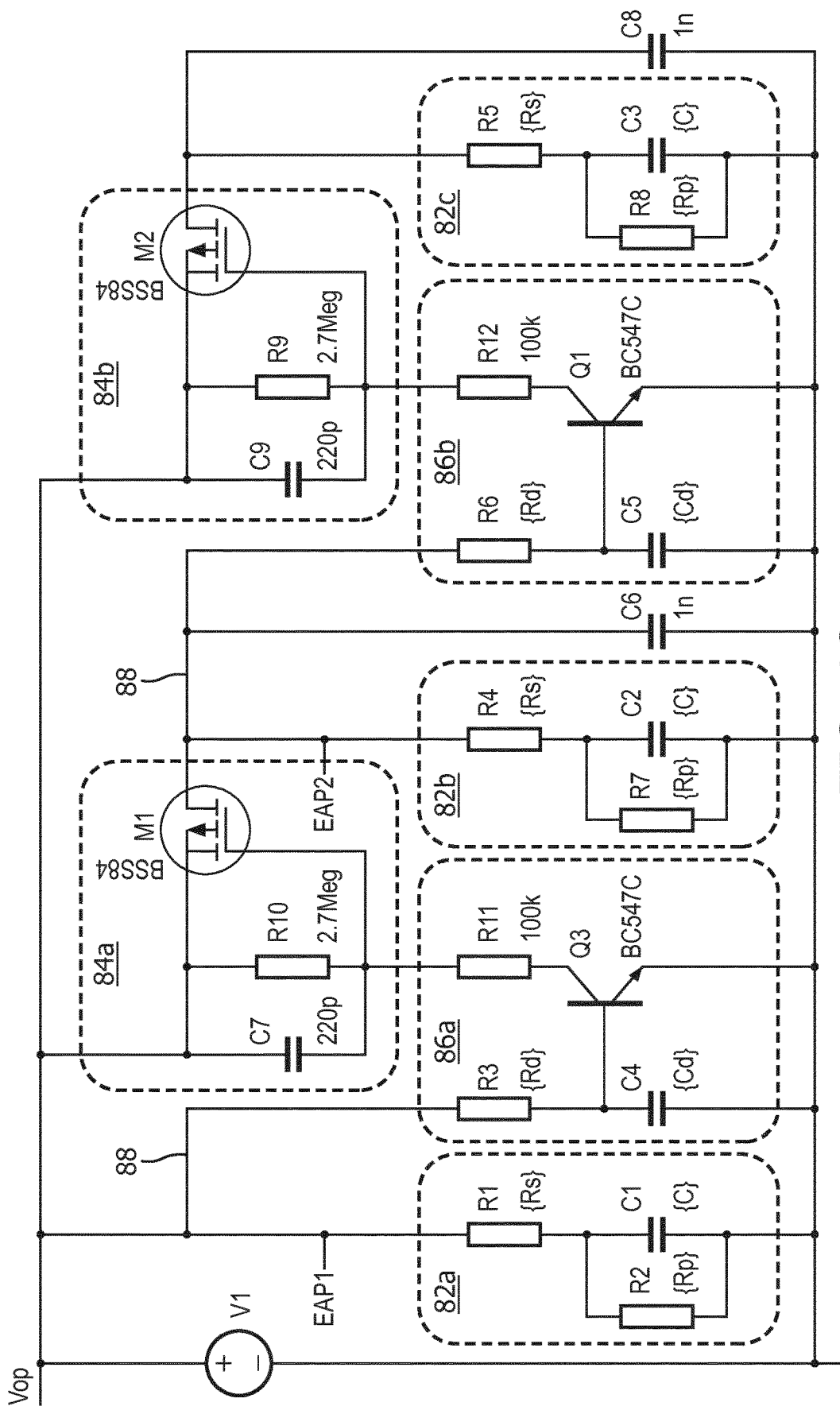
FIG. 12 shows an example control circuit for controlling an array of actuator elements in accordance with one or more embodiments of the invention.

An example circuit is shown in FIG. 12. This circuit is suitable in particular for embodiments in which actuator elements 42 are sequentially activated in series. For purposes of illustration, the circuit of FIG. 12 assumes there to be three actuator elements to be activated. However, it will be recognized that the circuit may be expanded to service activation of any number of actuator elements in series. Furthermore, for purposes of illustration, the actuator elements are assumed to be electroactive polymer based elements actuable by application of an electric field across a layer of EAP.

As is known in the art, an EAP actuator may be modelled electrically by a capacitor and resistor connected in parallel, both connected in series to a further resistor. The circuit of FIG. 12 comprises three such EAP actuator elements, indicated by dashed boxes 82a, 82b and 82c. Each actuator circuit 82 is driven by a DC signal, for example having a voltage at or in the order of 200V (which is assumed to be the maximum driving amplitude of the EAPs). The EAP actuator circuits 82 are connected to a common ground. No additional wires need be connected to each EAP actuator circuit, apart from a single serial connection 88 (which acts as trigger line) running between actuator elements.

In the example shown, the first EAP actuator element 82a will be activated as soon as operation voltage $V_1$ is supplied.

In order to activate the second 82b and third 82c actuator elements, two simple circuit blocks are connected to each: an electronic switching circuit (circuits 84a and 84b) and a timing circuit (circuits 86a and 86b). The switching circuit 84 supplies the EAP actuator element 82 with energy depending upon the state of the timing circuit 86. The timing circuit consists of a simple RC-timer followed by a transistor switch. If EAP actuator (n−1) is activated, the timer circuit n will activate the switch n after a particular time delay, the delay being defined by the RC time constant $\tau = Rd \cdot Cd$, where Rd and Cd are the resistance and capacitance respectively of the resistor and capacitor of the RC circuit. For illustration, values shown in the example circuit have been chosen to realize a delay of 200 ms. Once actuator element n is activated, the same sequence will occur for actuator element (n+1), with this element being activated after a time delay instigated by timer circuit n+1.

Figure 13:
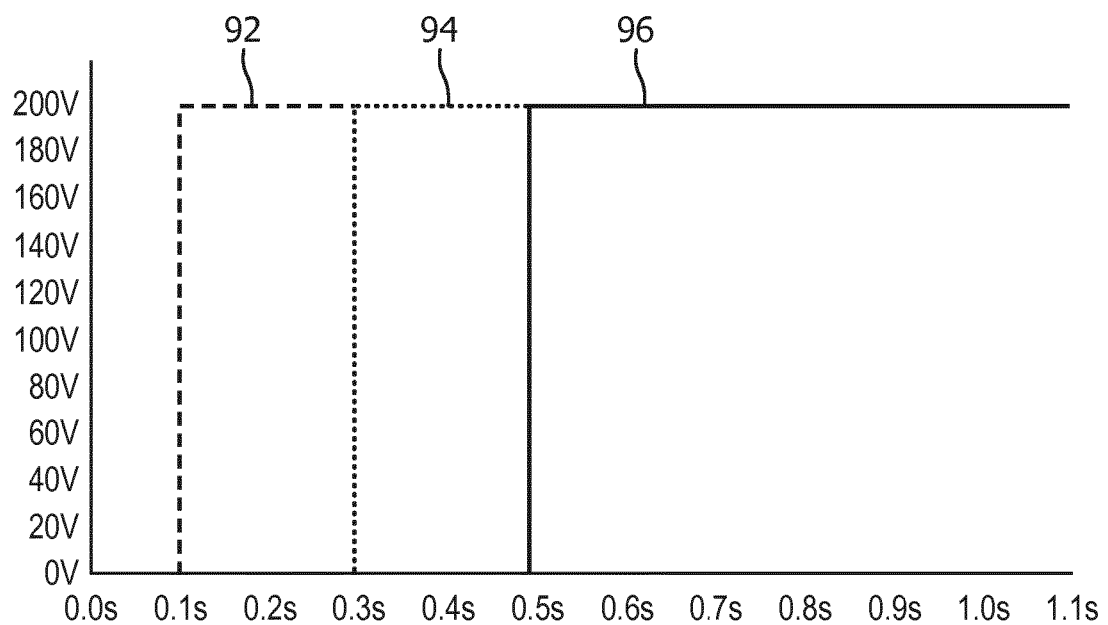
FIG. 13 shows the resultant voltage applied through actuator element as a function of time using the example control circuit of FIG. 12.

FIG. 13 shows the voltage (y-axis, V) applied through each EAP actuator element 82 of the exemplary circuit of FIG. 12 as a function of time (x-axis, seconds). Line 92 shows the voltage through actuator element 82a, line 94 shows the voltage through actuator element 82b and line 96 the voltage through actuator element 82c. It can be seen that there is a 200 ms delay in current being provided through each of the actuator elements.

Adaptations or extensions to the example circuit of FIG. 12 are possible and would be apparent to a person skilled in the art, e.g. extending the circuit to accommodate EAP elements, or adding extra timing and switching circuits to deactivate one or more actuator elements after a certain time delay. By adjusting the timings (by tuning Rd and Cd of the timings circuit) also other actuation profiles and behaviors may be created.

As noted above, embodiments of the present invention may advantageously be applied for so called organ-on-a-chip applications, and in further examples for storage of liquids that require some kind of continuous agitation, such as for instance blood.

Although in various examples above, actuator arrangements 38 have been shown comprising a single layer of EAP material having a segmented backing 52 to induce localized bending, other configurations are possible. In further examples, an actuator arrangement may comprise an array of individually formed actuating elements, distributed on a carrier layer, and individually actuable by electrical stimulation. Each may be provided with a pair of electrodes surrounding the element for applying electrical stimulation. Each element may comprise at least one layer of EAP material, and preferably comprises a resilient backing layer to induce bending.

In the case of a single layer of EAP having a segmented backing to divide the layer into individual actuator elements, individualized control of actuator elements can be achieved by providing individually controllable electrodes to each respective actuator element. Each set of electrodes induces local stimulation at only the location of the actuator element in question, thereby providing individualized actuation of the particular actuator element.

Materials suitable for the electroactive polymer of the electroactive polymer actuator arrangement are known. Suitable electro-active polymers for instance include, but are not limited to, the sub-classes: electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to: Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to: acrylates, polyurethanes, silicones.

The sub-class conjugated polymers includes, but is not limited to: polypyrrole, poly-3,4-ethylenedioxythiophene, poly(p-phenylene sulfide), polyanilines.

In all of these examples, additional passive layers may be provided for influencing the electrical and/or mechanical behavior of the EAP particle in response to an applied electric field.

Each EAP particle may be sandwiched between electrodes. The electrodes may be stretchable so that they follow the deformation of the EAP material. Materials suitable for the electrodes should be ultrasound-transmissive and include for instance thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS).

If the electrodes are arranged in a non-symmetric configuration, the imposed voltage can induce all kinds of deformations such as twisting, rolling, torsioning, turning, and non-symmetric bending deformation.

As discussed above, some embodiments of the actuator arrangement aspect of the present invention make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

Any reference signs in the claims should not be construed as limiting the scope.

The invention claimed is:

1. A biological cell preservation arrangement comprising:
    a chamber being a fluidically closed fluid retaining space configured to retain a volume of fluid and retain biological cells in the volume of fluid;
    an impermeable deformable membrane within the chamber, and
    an electroactive polymer actuator arrangement configured to deform the deformable membrane, and a controller that controls the electroactive polymer actuator arrangement to change in a surface topology of the deformable membrane, wherein the controller changes the surface topology in a sequence of topology changes to produce a flow of the fluid in a direction that corresponds to a direction of the sequence of topology changes and is parallel to a plane of the deformable membrane.

2. The biological cell preservation arrangement of claim 1, wherein the controller is configured to effect regular or recurrent changes in the surface topology of the membrane on a continuous basis.

3. The biological cell preservation arrangement of claim 1, wherein the deformable membrane at least partially bounds the fluid retaining space.

4. The biological cell preservation arrangement of claim 1, wherein each surface topology change comprises surface deformations of the deformable membrane directed inward and outward of the fluid retaining space, the inward deformations being balanced volumetrically with the outward deformations such that there is a zero net change in the volume of the fluid retaining space before and after each topology change.

5. The biological cell preservation arrangement of claim 1, wherein the electroactive polymer actuator arrangement comprises an array of actuator elements, each comprising an electroactive polymer that is actuable to undergo a bending action.

6. The biological cell preservation arrangement of claim 5, wherein
the electroactive polymer actuator arrangement comprises an actuating layer, the actuating layer comprising the array of actuator elements, and
the electroactive polymer actuator arrangement comprises a layer of electroactive polymer and wherein each actuator element comprises a segment of the layer of electroactive polymer.

7. The biological cell preservation arrangement of claim 5, wherein each actuator element is electrically drivable to move between a first stable actuation position and a second stable actuation position.

8. The biological cell preservation arrangement of claim 1, wherein
the arrangement is a cell culturing arrangement, and
the pattern of fluid flow is for enabling nutrient replenishment of cells located at or proximal to the deformable membrane.

9. The biological cell preservation arrangement of claim 8, wherein
the arrangement comprises a substrate for culturing biological cells, the substrate being arranged within the chamber, and
the substrate is adapted to retain the cells on the substrate, wherein the substrate forms at least part of a chip for organ-on-a-chip cell growth.

10. The biological cell preservation arrangement of claim 1, wherein the arrangement is a blood storage arrangement and wherein the deformable membrane is for agitating blood stored within the fluid retaining space to prevent activation of platelets within the blood and/or to prevent coagulation of the blood, and wherein the blood storage arrangement comprises a blood storage bag, the bag forming the chamber.

11. The biological cell preservation arrangement of claim 10, wherein
the deformable membrane forms at least a portion of an enclosing wall of the fluid retaining space, and the electroactive polymer actuator arrangement comprises an actuation layer comprising an electroactive polymer, the layer being disposed in engaging fashion against the deformable membrane forming a wall of the fluid retaining space for deforming the membrane.

12. The biological cell preservation arrangement of claim 1, wherein the electroactive polymer actuator arrangement comprises an electrostrictive electroactive polymer material.

13. The biological cell preservation arrangement of claim 5, wherein the controller is adapted to recurringly control the actuator elements to actuate in a cascading fashion wherein the actuators are actuated in sequential consecutive groups, each actuated group being larger than the previously actuated group.

14. The biological cell preservation arrangement of claim 1, wherein:
the electroactive polymer actuator arrangement comprises a first actuator arrangement and a second actuator arrangement,
the first actuator arrangement is arranged on a first surface of the chamber,
the second actuator arrangement is arranged on a second surface of the chamber, opposite the first surface,
the controller changes the topology of the first surface to induce the flow of the fluid in a first direction,
the controller changes the topology of the second surface to induce the flow of the fluid in a second direction,
wherein the second direction is opposite the first direction, thereby causing a circular flow of the fluid within the chamber.

15. A biological container comprising:
a fluidically closable chamber comprising a fluid retaining space configured to retain a volume of fluid comprising biological material;
wherein the chamber comprises one or more deformable membranes;
a first electroactive polymer actuator arrangement;
a second electroactive polymer actuator arrangement; and
a controller;
wherein the first and second electroactive polymer actuator arrangements are situated at opposing first and second surfaces of the chamber;
wherein the controller is configured to control the first and second electroactive polymer actuator arrangements to change a first topology of the first surface and a second topology of the second surface;
wherein the controller is configured to change the first topology and the second topology to induce a first flow of the fluid in a first direction parallel to the first surface, and a second flow of the fluid in a second direction parallel to the second surface;
wherein the first direction is opposite to the second direction, thereby inducing a circular flow of the fluid within the chamber.

16. The biological container of claim 15, wherein each of the first and second electroactive polymer actuator arrangements comprises an array of actuator elements, wherein each actuator element comprises an electroactive polymer that is actuable to undergo a bending action.

17. The biological container of claim 16, wherein the controller:
selectively controls the actuator elements of the first electroactive polymer actuator arrangement in a first ordered sequence that causes the fluid flow in the first direction to be in a direction corresponding to the first ordered sequence, and selectively controls the actuator elements of the second electroactive polymer actuator arrangement in a second ordered sequence that causes the fluid flow in the second direction to be in a direction corresponding to the second ordered sequence.

18. The biological container of claim 17, wherein the first ordered sequence and second ordered sequence provide changes to the first topology and the second topology that maintain a substantially constant volume of the chamber.

\* \* \* \* \*